United States Patent [19]

Lasner et al.

[11] 4,369,787
[45] Jan. 25, 1983

[54] METHOD OF CUTTING A SUTURE

[75] Inventors: Jeffrey I. Lasner, Purchase; Francisco H. Aleixo, Tarrytown, both of N.Y.

[73] Assignee: Laschal Instruments Corp., North Tarrytown, N.Y.

[21] Appl. No.: 202,063

[22] Filed: Oct. 30, 1980

Related U.S. Application Data

[60] Division of Ser. No. 945,809, Sep. 26, 1978, Pat. No. 4,271,838, which is a continuation-in-part of Ser. No. 893,582, Apr. 5, 1978, abandoned, which is a continuation-in-part of Ser. No. 872,388, Jan. 26, 1978, abandoned.

[51] Int. Cl.$^3$ .................. A61B 17/32; A61F 17/32
[52] U.S. Cl. ..................................... 128/318; 128/305
[58] Field of Search ............... 128/305, 318, 334 R; 30/200, 233

[56] References Cited

U.S. PATENT DOCUMENTS

| | | | |
|---|---|---|---|
| 3,054,182 | 9/1962 | Whitton, Jr. | 128/305 |
| 3,328,876 | 7/1967 | Hoppe | 128/305 |
| 3,364,572 | 1/1968 | Hoppe | 128/305 |
| 3,364,573 | 1/1968 | Hoppe | 128/305 |
| 3,372,477 | 3/1968 | Hoppe | 128/305 |
| 4,034,473 | 7/1977 | May | 128/305 |
| 4,053,979 | 10/1977 | Tuthill et al. | 128/305 |

Primary Examiner—Michael H. Thaler
Assistant Examiner—C. W. Shedd
Attorney, Agent, or Firm—Jordan B. Bierman; Linda Bierman

[57] ABSTRACT

A method of cutting a suture at least partly disposed in tissue and bearing a knot formed in the suture, wherein the suture is introduced into the slot of a suture cutter having a slotted member of a predetermined depth and a cutting blade relatively moveable with respect to the slotted member, the cutter is moved along the suture until the member contacts the knot, and the cutting blade is relatively moved across the slot to shearingly contact the suture such that a stub substantially equal in length to the depth of the slotted member remains on the suture adjacent the knot.

2 Claims, 11 Drawing Figures

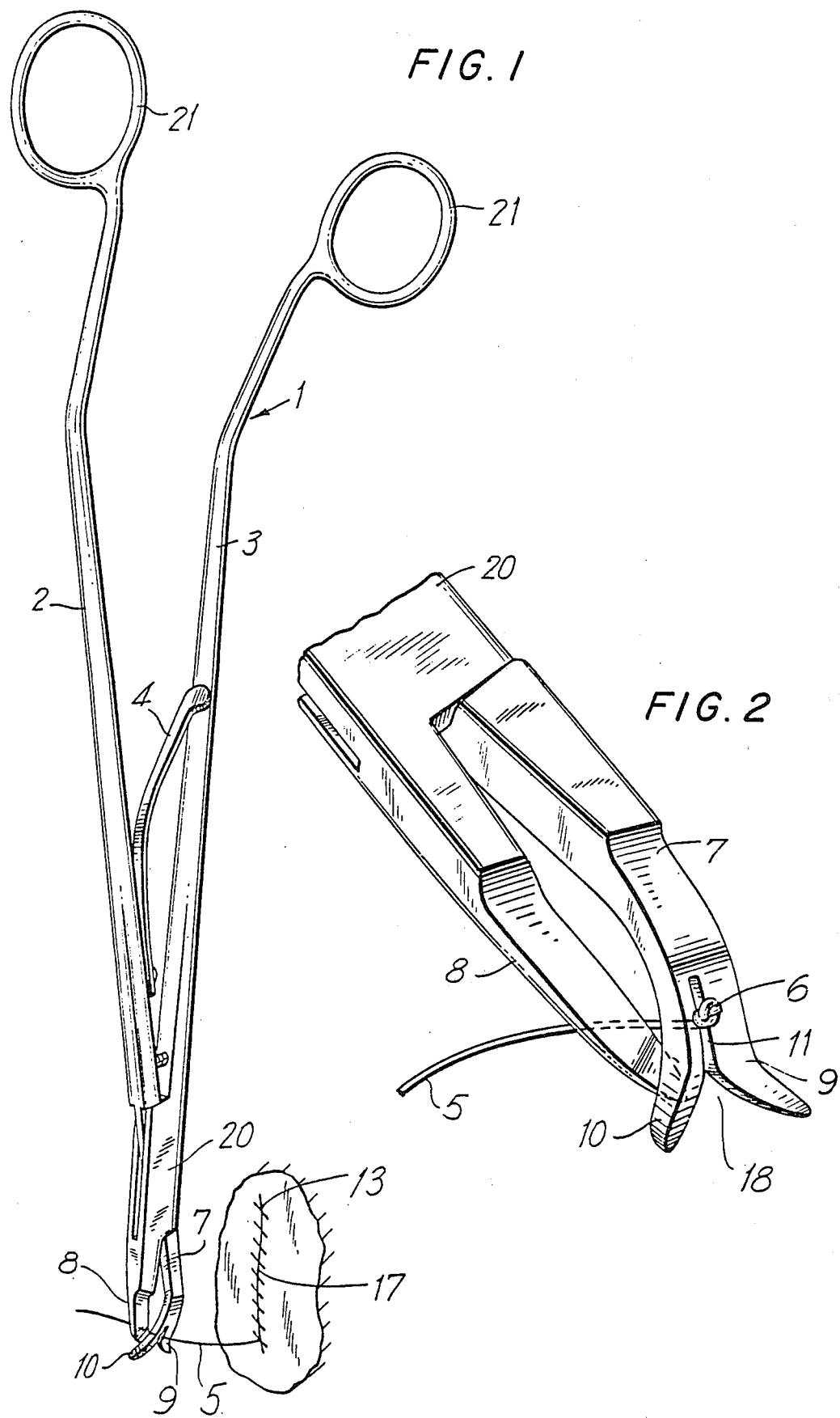

METHOD OF CUTTING A SUTURE

BACKGROUND OF THE INVENTION

This application is a division of Ser. No. 945,809, now U.S. Pat. No. 4,271,838 filed Sept. 26, 1978, which is a continuation-in-part of Ser. No. 893,582 now abandoned, filed Apr. 5, 1978, which is a continuation-in-part of Ser. No. 872,388 now abandoned, filed Jan. 26, 1978.

The present invention is directed to an improvement in surgical instruments, and more specifically to suture cutters.

Suture cutters as such have been known in the art for many years. They are used to sever the end of the suture after the surgeon has knotted it. A predetermined length of stub should be left for best results. If the stub is too short, there is a danger that the knot will loosen. If the stub is too long, it may interfere with surrounding tissue. Therefore, getting the length correct is one of the problems of the surgeon.

In addition, since sutures are usually tied inside the body, the risk of cutting tissue or a blood vessel is quite substantial. The surgeon must exercise considerable care in order to avoid doing this. The problem is compounded when the suture is keep in the body or the patient is particularly obese.

The present invention is intended to overcome the deficiencies of the prior art, and to provide a suture cutter which is simple and virtually foolproof in its operation. By the proper use of the present invention, even a semi-skilled assistant can cut the sutures quickly, easily, and safely.

In practicing the present invention, there is provided a suture cutter comprising a first shank and a second shank. The shanks are pivotally connected to one another at a point intermediate their ends, thus forming a scissor-like arrangement. One end of the pair of shanks constitutes a handle. The first shank terminates in a member at the end thereof remote from the handle and the second shank terminates in a blade at the end remote from the handle. The blade is provided with a knife edge and a back remote from the edge. In this manner, the blade is adapted to shearingly contact the member.

The member itself is of a predetermined depth and comprises an arm, an element, and a slot therebetween. The slot is large enough to receive the suture but is too small to permit a knot in the suture to pass therethrough.

The blade and knife edge contact the element on the "top" or side away from the incision. As a result, the depth of the member determines the length of stub which will be left after cutting.

In a preferred form of the device, the arm is relatively rigid and the element is flexible. Therefore, the element is capable of moving towards the arm as the blade rubs against it during the cutting operation. This causes, in the most preferred form of the device, the element to contact the arm and secure the suture within the slot. For best results, the element should be spring biased away from the arm and a hole provided in the slot to receive the suture. The hole, like the slot itself, is too small to permit a knot in the suture to pass therethrough.

For best results and simplest operation, the slot is provided with an access opening so that the suture can be readily inserted. It is particularly helpful if the access opening is flared for ease of insertion of the suture.

An advantageous form of the device includes a face on the blade located adjacent the surface of the element. The face is inclined toward the element so that the portion of the face near the knife edge is further from the element than the portion near the back. As a result, the pressure on the element increases as the knife edge moves over the element and cuts the suture. This insures that the element closes the slot and holds the suture in position.

The operation of the instrument is extremely simple and foolproof. After the surgeon has tied the suture knot, the free suture is inserted into the slot through the flared opening. This can be done near the upper end of the suture for convenience. The instrument is then slid down along the suture until the underside of the member contacts the knot. The handles are then brought together in the usual manner, and the knife edge cuts the suture.

As can easily be seen, the depth of the member determines the length of the stub of suture which will be left. Therefore, it is only necessary to design the cutter so that the member has a thickness corresponding to the desired length of suture stub. For example, 3 to 3.5 mm is appropriate for silk sutures, 4.5 to 5 mm is proper for gut, etc.

As a modified method of using the device, the instrument may be partially closed before sliding it along the suture so that the blade bears against the element and causes it to close the slot. The suture is held in the hole by this means. In this way, there is no real chance that the suture can slip out of the slot.

In another modification of the present invention, the suture cutter is mounted on the same "forceps" as constitute a surgical needle holder. Thus, without changing instruments or releasing the knot he is tying, the surgeon can make the stitch, tie the knot, and cut off the excess suture leaving precisely the correct amount of stub.

As can be seen from the foregoing, it is virtually impossible for the surgeon to inadvertently cut any tissue, blood vessels, organs, etc. In fact, the suture can be safely cut even if the surgeon cannot see the knot.

BRIEF DESCRIPTION OF THE DRAWINGS

In the accompanying drawings, constituting a part hereof and in which like reference characters indicate like parts:

FIG. 1 is an overall, partly diagrammatic view of the device;

FIG. 2 is an enlarged bottom view in perspective of the operative portion of the device;

DETAILED DESCRIPTION OF THE PREFERRED EMBODIMENTS

Figure 3:
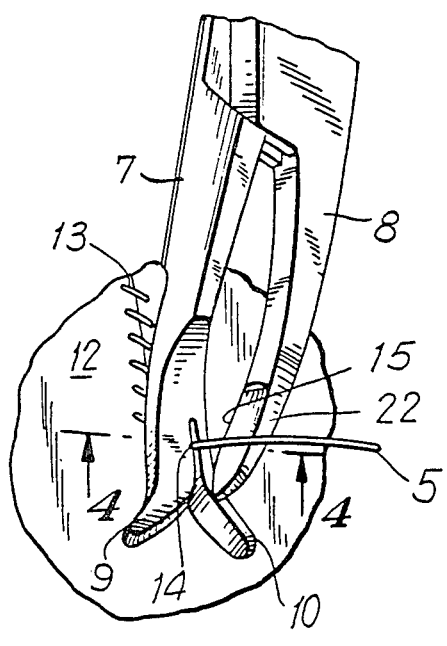
FIG. 3 is an enlarged top view of the operative portion of the device as it is used.
Figure 5:
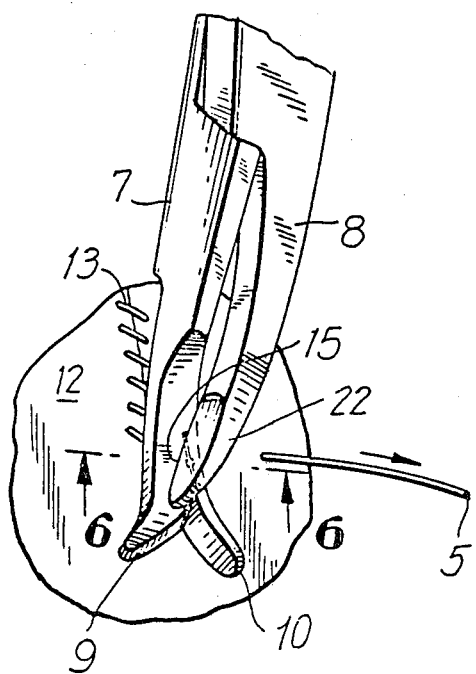
FIG. 5 is a view similar to FIG. 3 after the suture has been cut.

The suture cutter of the present invention is shown generally at 1. It comprises a first shank 2 and a second shank 3. Shanks 2 and 3 are pivotally connected at point 20 intermediate their ends. Spring 4 is provided to bias cutter 1 in its open position.

Shank 3 terminates, on the opposite side of point 20 from handle 21, in blade 8 having a knife edge 15. Shank 2 terminates, at the end opposite handle 21, in member 7.

Member 7 bifurcates adjacent its end into arm 9 and element 10. Knife edge 15 is adapted to pass shearingly over element 10 and arm 9 to cut suture 5 which is placed in hole 14 in slot 11. Access opening 18 is provided at the end of slot 11 so that suture 5 can easily be inserted herein.

Figure 4:
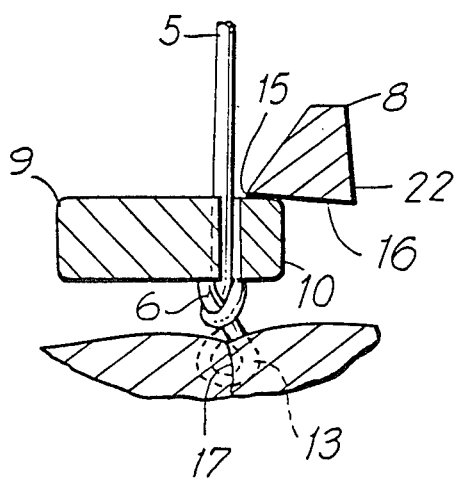
FIG. 4 is a cross-sectional view along the lines 4—4 of FIG. 3.
Figure 6:
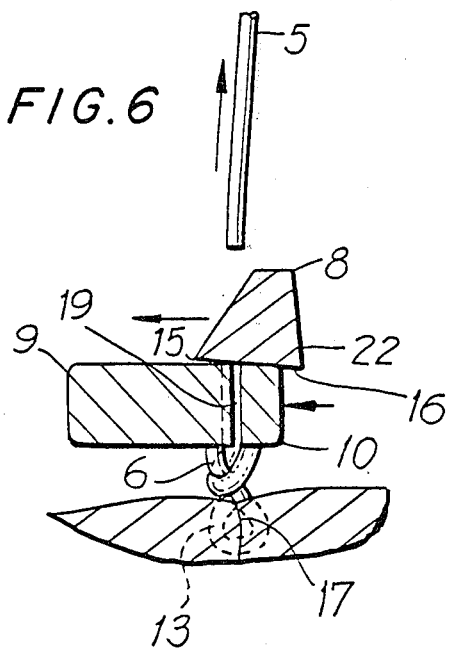
FIG. 6 is cross-sectional view along the lines 6—6 of FIG. 5.

Referring more specifically to FIGS. 4 and 6, face 16 of blade 8 is inclined with respect to element 10. Thus, as blade 8 is moved towards suture 5, the pressure of face 16 on element 10 is increased. This insures that element 10 will move to the position shown in FIG. 6 and hold suture 5 securely as it is being cut. After cutting, stub 19 is left on suture 5.

In using the instrument, incision 17 is closed by means of stitches 13 in skin 12. Before cutting, suture 5 extends from each stitch. Suture 5 is then inserted into slot 11 and hole 14 through access opening 18 in member 7. Cutter 1 may then be partially closed so that blade 8 and knife edge 15 move towards suture 5, without contacting it. This causes element 10 to meet arm 9 and secure suture 5 in hole 14. In the preferred form of the device, inclined face 16 puts increasing pressure on element 10 to affirmatively cause it to close slot 11.

The operative end of cutter 1 is moved along suture 5 until the underside of arm 9 and element 10 contact knot 6 in suture 5. This can be done entirely by feel and it is not necessary to actually see either knot 6 or incision 17.

Cutter 1 is then fully closed causing blade 8 and knife edge 15 to shear off suture 5, leaving stub 19 of the proper, predetermined length.

Figure 7:
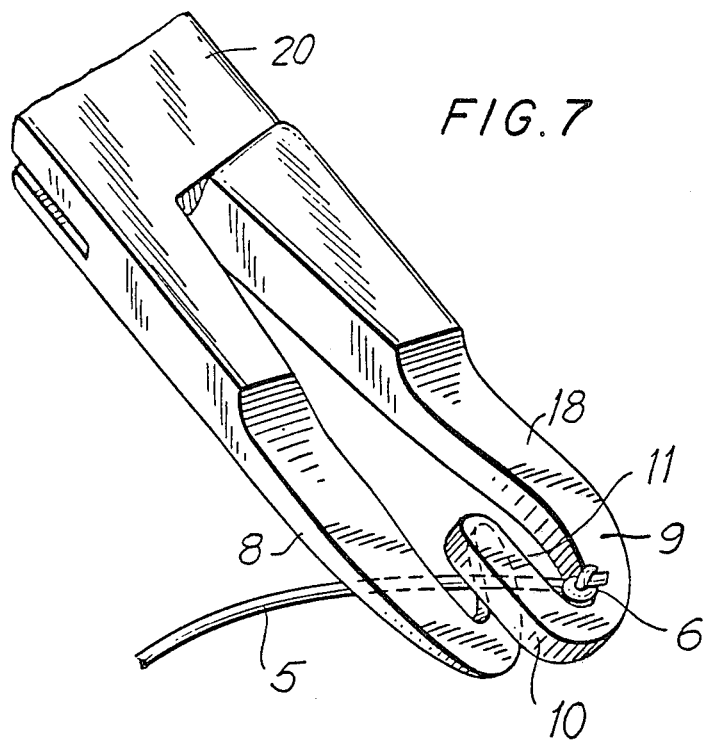
FIG. 7 is a view similar to that of FIG. 2 of another embodiment of this invention.

A modified form of the invention is shown in FIG. 7. Here slot 11 is provided with access opening 18 facing the user of the device. This permits introduction of suture 5 into slot 11 through access opening 18 from the side of the cutter away from the tissue. For some surgical procedures this form has been found particularly advantageous.

Figure 8:
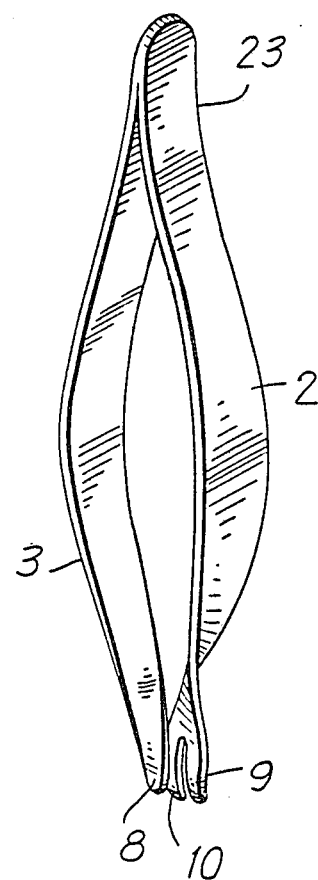
FIG. 8 is a perspective view of the "tweezer" form of the device.

It will also be appreciated that the manner of achieving the relative motion between blade 8 and member 7 is not critical. In the principal form of the invention, this has been described as a privoted structure similar to a pair of scissors. An alternative form is shown in FIG. 8. Shanks 2 and 3 are connected by tweezer 23 thereby permitting blade 8 to shearingly contact element 10 and arm 9 in the same manner as in the other forms of the device. This embodiment has been found most useful in eye surgery and similar delicate surgical procedures.

Figure 9:
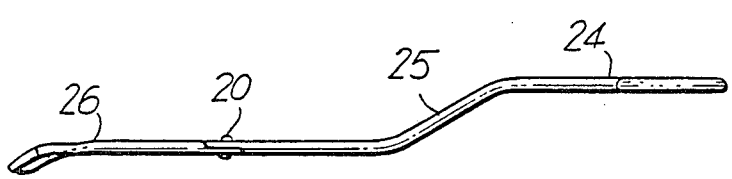
FIG. 9 is a schematic view of the "offset" form of the invention.

Sometimes the angle of use of the device is such that the head interferes with the vision of the surgeon. In such situations, the embodiment schematically shown in FIG. 9 may be useful. Handle section 24 is in one plane and head section 26 is in another plane. Sloping section 25 connects the two. In this form of the device, the surgeon has a better view of what he is doing and, for certain applications, will find it more convenient to use. While this embodiment has been illustrated in connection with the scissor-like form of the device, it is, of course, equally applicable to the tweezer-like device.

Figure 10:
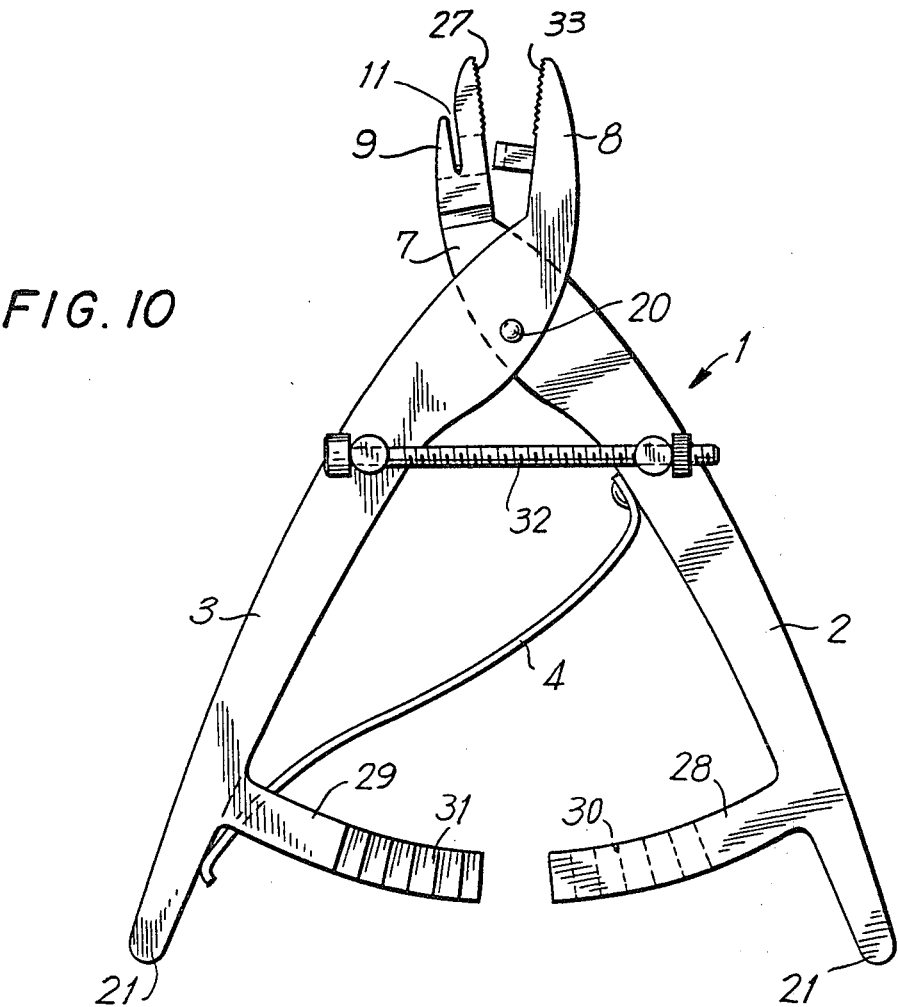
FIG. 10 is a plan view of the combination suture cutter and needle holder modification.
Figure 11:
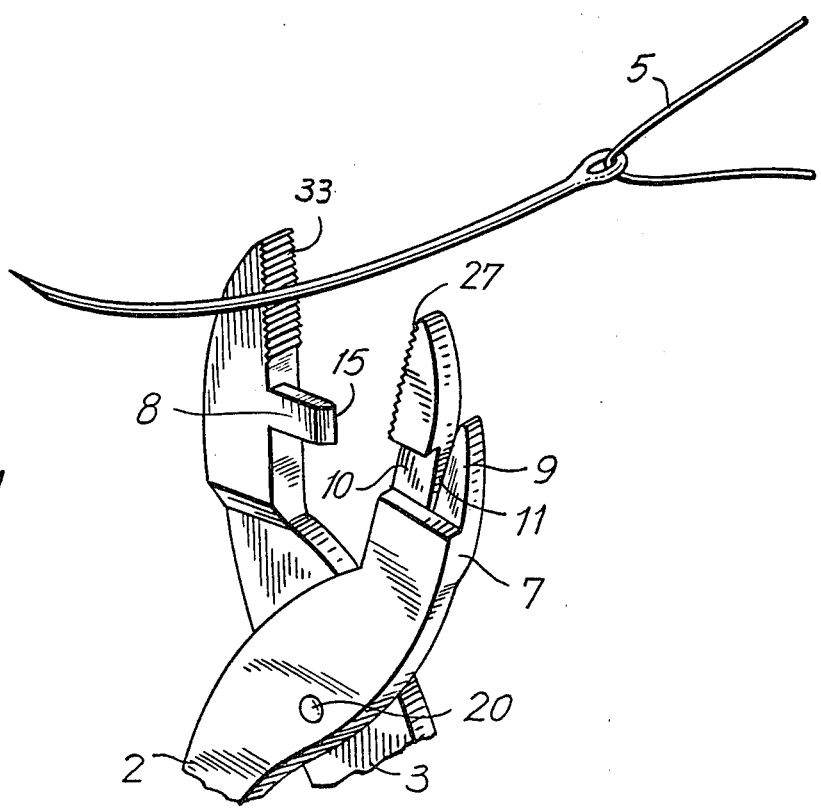
FIG. 11 is an enlarged view of the head of the suture cutter of FIG. 10.

Referring more specifically to FIGS. 10 and 11, a further modification of the present invention includes the provision of a needle holder as part of the single tool. The configuration of the device is generally the same as the other forms of the invention, but there are also provided needle-gripping areas 33 and 27 on blade 8 and member 7, respectively. Knife edge 15 is of a slightly different shape and bears against element 10 and arm 9.

The device is also provided with first grip 28 and second grip 29 on shanks 2 and 3, respectively. Grip 28 carries first ratchet 30 and grip 29 carries second ratchet 31. Ratchets 30 and 31 face each other and are adapted to inter-engage.

As the device is closed and the needle gripped between areas 27 and 33, ratchets 30 and 31 overlap one another and interlock. This holds the device in the closed position against the tension of spring 4. The surgeon can then tie the knot without danger of inadvertently releasing the needle.

After the knots have been completed, the needle is released, the thread is inserted into slot 11, and the device is closed. This causes knife edge 15 to shear off the suture in a similar manner to the other embodiments of this invention. As a result, a stub equal in length to the depth or thickness of arm 10 and element 11 is left. This form of the device enables the surgeon to make the stitch, tie the knot, and cut the thread without changing instruments.

As an additional safety feature, limit screw 32 is provided. This adjustable screw prevents the device from opening wider than is desired. For best results, knife edge 15 should remain in contact with arm 9 or element 10 at all times. This prevents any tissue from being caught between knife edge 15 and element 10.

It is one of the features of the present invention that, in its most preferred form, the instrument is so designed that knife edge 15 is not permitted to extend beyond member 7. This prevents tissue from being inadvertently caught between the knife edge and the member. Moreover, due to the inherent nature of the scissor-like action of the instrument, the blade is self-sharpening. Abrasion against the member acts to hone the edge and maintain it in sharp condition.

While only a limited number of embodiments of this invention have been specifically described, it is, nonetheless, to be broadly construed and not to be limited except by the character of the claims appended hereto.

What is claimed is:

1. A method of cutting a suture at least partly disposed in tissue and bearing a knot formed in the suture, comprising the steps of:
   introducing the suture into the slot of an elongated suture cutter having a slotted member of a predetermined depth and a cutting blade relatively moveable with respect to the slotted member and substantially perpendicular to the elongation of the suture cutter, said introduction of the suture into the slot being performed by moving the suture cutter longitudinally parallel to its elongation so that the suture is thereby introduced into the slot which extends along the direction of elongation of the suture cutter;

moving the suture cutter along the suture within the slot until the member contacts the knot; and moving the cutting blade across the slot and substantially perpendicular to the elongation of the suture cutter so as to cut the suture and automatically leave on the suture and adjacent the knot a stub substantially equal in length to the depth of the slotted member.

2. A method of cutting a suture in accordance with claim 1 wherein relative movement of the cutting blade and slotted member causes the blade to bear against the member and close the slot in advance of suture shearing movement of the blade across the slot, said method further comprising:

relatively moving the cutting blade into bearing relation against the member so as to close the slot after said introduction of the suture into the slot and prior to said moving of the suture cutter along the suture into contact with the knot, whereby the suture is prevented from slipping out of the slot as the suture cutter is moved along the suture.

* * * * *